United States Patent [19]

Paulson et al.

[11] 4,307,726
[45] Dec. 29, 1981

[54] DIAGNOSTIC EVALUATION, MEASUREMENT, AND ANALYSIS OF FUNCTIONAL ACTIVITY IN BODY ORGANS THAT UTILIZE TRANSMEMBRANE ION POLARIZATION AND DEPOLARIZATION

[76] Inventors: James C. Paulson, 519 30th Ave.; Robert D. Pfeifer, 695 29th Ave., both of San Mateo, Calif. 94403

[21] Appl. No.: 71,992

[22] Filed: Sep. 4, 1979

Related U.S. Application Data

[63] Continuation-in-part of Ser. No. 899,571, Apr. 24, 1978, abandoned.

[51] Int. Cl.³ .............................................. A61B 5/05
[52] U.S. Cl. ................................................... 128/653
[58] Field of Search ................................. 128/630, 653

[56] References Cited

U.S. PATENT DOCUMENTS

| | | | |
|---|---|---|---|
| 2,276,996 | 3/1942 | Milinowski1 | 28/422 |
| 2,804,069 | 8/1957 | Schwamm et al. | 128/653 |
| 3,483,860 | 12/1969 | Namerow | 128/653 |
| 3,789,832 | 2/1974 | Damadian | 128/653 |
| 3,789,834 | 2/1974 | Daroux | 128/1.3 |
| 3,915,151 | 10/1975 | Kraus | 128/419 R |
| 4,078,553 | 3/1978 | Duroux | 128/694 |
| 4,135,131 | 1/1979 | Larsen et al. | 128/653 |

FOREIGN PATENT DOCUMENTS

| | | | |
|---|---|---|---|
| 2618424 | 11/1976 | Fed. Rep. of Germany | 128/630 |
| 2716672 | 11/1977 | Fed. Rep. of Germany | 128/630 |

OTHER PUBLICATIONS

Robinson, J. E. et al., "Microwave Heating of Malignant Mouse Femour and Tissue Equivalent Phantom Systems", Jrnl. of Microwave Pwr., vol. 11, No. 2, pp. 87–98.

Primary Examiner—Robert W. Michell
Assistant Examiner—Francis J. Jaworski
Attorney, Agent, or Firm—Julian Caplan

[57] ABSTRACT

Beams of coherent microwaves or other frequencies of highly directional electromagnetic radiation are passed through the living human body to detect and provide a quantitative analysis of functional activity in the central nervous system and/or in muscle tissue such as that of the heart. Organs to be analyzed are situated in the space of an electrostatic field of oscillating intensity. The directional beam is passed through a body organ situated in this way. The method is of use in detecting degenerative subcortical disease in the brain (e.g., Sulphatide Lipidosis), tissue damage to nerve fibers due to toxic chemicals, and other types of tissue-based functional abnormality. Functional condition of brain and heart generally can be readily analyzed without exposure to ionizing radiation.

15 Claims, 5 Drawing Figures

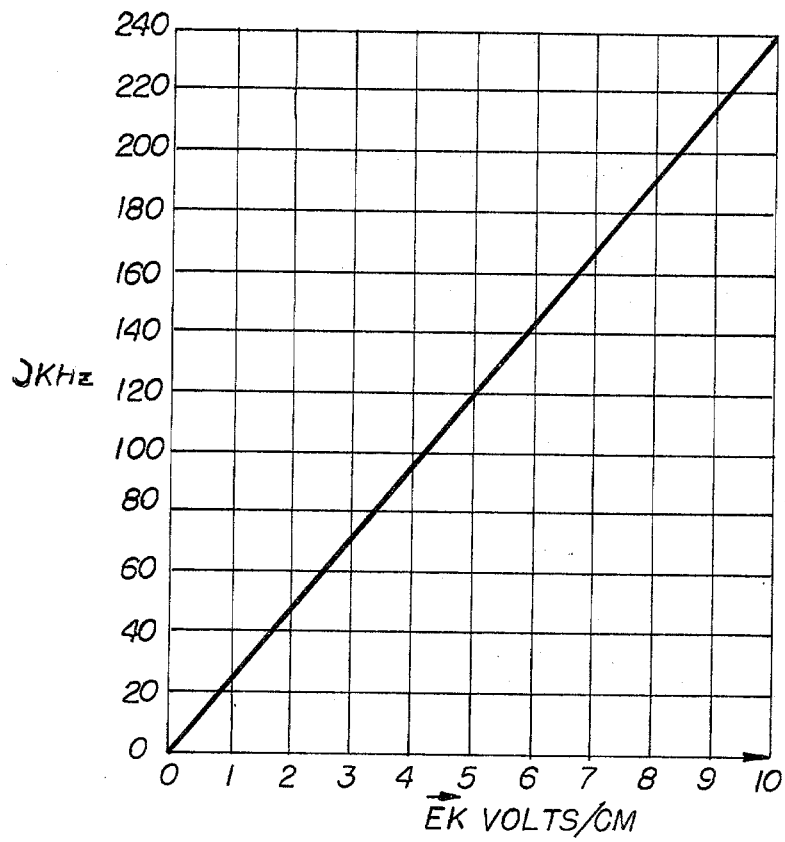

Fig. 3

| MODE | FREQUENCY | PATH | INTERPLATE $\vec{E}$ | WAVE FORM | | INTERPLATE DISTANCE | PLATE VOLTAGE | FREQUENCY |
|---|---|---|---|---|---|---|---|---|
| DC 1 | ≪250Hz 239.4 Hz | 12 ft | ≪Ex 10 VOLTS/CM | PLATE SQUARE | PHASE MODULATION ASYMMETRICAL SINE | 40 CM | ≪x 400 VOLTS | <γ |
| AC 2 | >250 Hz 23.9 KHz | 12 ft | >Ex<10⁴V/CM 10³VOLTS/CM | SQUARE | ASYMMETRICAL SINE | 40 CM | >X<Vb 40 K VOLTS | <γ |
| DC 2 | >250 Hz 23.9 KHz | 12 ft | >Ex<10⁴V/CM 10³VOLTS/CM | SQUARE | ASYMMETRICAL SINE | 40 CM | >X<Vb 40 K VOLTS | <γ |
| AC 1 | ≪250Hz 239.4 Hz | 12 ft | ≪Ex 10 VOLTS/CM | SQUARE | ASYMMETRICAL SINE | 40 CM | ≪x 400 VOLTS | <γ |

Fig. 4

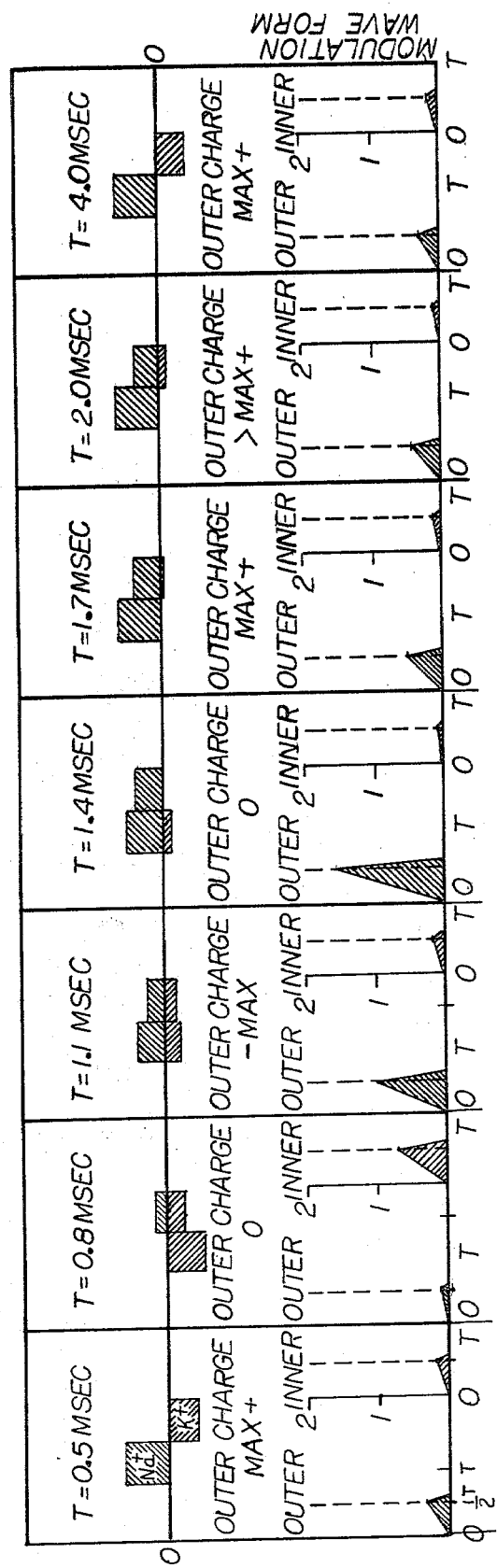

DIAGNOSTIC EVALUATION, MEASUREMENT, AND ANALYSIS OF FUNCTIONAL ACTIVITY IN BODY ORGANS THAT UTILIZE TRANSMEMBRANE ION POLARIZATION AND DEPOLARIZATION

This application is a continuation-in-part of co-pending Ser. No. 899,571, filed Apr. 24, 1978, now abandoned.

BACKGROUND OF THE INVENTION

1. Field of Invention

The invention's purpose is to produce a representation of functional activity in organs such as the brain and heart which representation is arranged according to space/time distribution and intensity, (x, y, z, t), (q). The variable q signifies intensity, a measurement of functional activity at a given location. Ready analysis of normal function in an intact organism and diagnosis of abnormality is thus facilitated.

2. Description of Prior Art

X-rays of specific organs, the EMI, and isotope absorption methods such as the Brain Scan are in common usage. Sonic transducers are a common diagnostic aid in relation to the brain and are more recently being applied to the heart. In the past few years, ion beams (e.g., proton beams) have been experimentally used for similar purposes. However, all of these methods are means for analyzing the distribution of tissue density variations. None of these methods provides a representation of the distribution of functional activity variation. Isotope absorption rate may be regarded as an exception to the last statement. However, isotope absorption rate is an indicator only of slow changes. The electroencephalogram and electrocardiogram indicate functional activity of brain and heart respectively. However, these means are not direct indicators of functional activity distribution in three dimensions. Further, specific localization of effect is not possible with either of these means. Three dimensional localization with the EEG is accomplished only by inference and includes uncertainty. Many types of functional activity occurring beneath the outermost layer of the cerebral cortex are not evidenced in the EEG. Methods for localizing and measuring subcortical functional activity other than the EEG exist. However, these methods are intrusive.

SUMMARY OF THE INVENTION

Electro-optical effects have been demonstrated and utilized in fields other than scanning the intact, living body (cf: Kerr Effect, Raman Effect, and Pockel's Effect). Alignment of dipoles will produce polarization and alteration of refractive intex (Kerr Cell). Oscillation of molecular dipoles will modulate refractive index (Pockel's Effect), and atomic resonance due to electromagnetic energy of the appropriate frequency will modulate the energy passing through the medium consisting of such atoms (Raman Effect). Polarized ions separated by membranes (ionic dipoles) are maintained along the periphery of neurons. These dipoles cover the inner and outer membrane surfaces of axons, dendrites, and cell bodies. When axon fibers become myelinated, these ionic dipoles become concentrated at the nodes of Ranvier. These dipoles are also distributed throughout myofibrils, as in the heart. While these types of cells are in a resting state dipoles remain static. These ion dipoles oscillate or vibrate in an electrostatic field when the field strength oscillates. The minimum value of applied field strength produces a small increment of separation between ions and the membrane surfaces along which they are gathered. These field effects occur parallel to the field direction. Resistance to vibration of these ions is reduced by the previously described increment of separation between ions and membrane surfaces. Variation of field strength between minimum and maximum values produces ionic dipole oscillation. For the average axon membrane thickness of 80 Å, dipole resonance frequency is calculated to be $4.6 \times 10^8$ $H_z$. Electric field oscillation at a rate greater than or less than resonance frequency induces or forces dipole vibration at the field's frequency. Thus, the refractive index of a medium containing ionic dipoles in relation to a directional beam (of wavelength in the microwave range, or some other range) is modulated. When such a directional beam passes through a body organ densely populated with these oscillating dipoles, modulation of the refractive index modulates the beam. The percentage of modulation of the directional beam is directly proportional to the multiplied product of the density of ionic dipoles and the corresponding volume penetrated by the beam. Functional activity level is directly proportional to time variant change of the percentage of modulation: Functional activity is defined as ionic depolarization. In operation of the system being presented, detection and measurement of the percentage of modulation is accomplished by the sensitive indicator consisting of measurement of phase change between waves in the directional beam before and after traversing the dipole containing medium.

OBJECTS OF THE INVENTION

It is an object of the invention to provide a method for distinguishing between normal and abnormal densities of ionic dipoles and fluctuations of these densities in the living human body and thereby to detect abnormalities of functional capacity and activity.

It is a further object of the invention to detect abnormalities of functional activity without utilizing surgical intrusion.

It is another object of the invention to provide early detection of brain tumors (indicated by localized impedance increases).

It is yet another object of the invention to detect the degree of development of myelin around axon fibers of the brain.

It is a further object of the invention to detect and represent degeneration of myelin and loss of Schwann cells.

It is still a further object of the invention to detect and represent impairment of transmembrane electrical activity (polarization and depolarization) in nerve tracts of the human brain.

It is still another object of the invention to detect and depict Parkinson's Disease and other abnormalities of neuron function due to abnormal function of the synapses.

It is an object of the invention to detect and display signals indicative of subcortical epilepsy which does not appear in the EEG.

It is another object of the invention to represent the space/time distribution of functional capacity and activity in the normal human brain and in the brains of animals so that individual differences can be studied.

It is an object of the invention to detect and represent abnormal distributions of functional capacity and activity in tissue of the heart (cardiac muscle).

It is an object of the invention to provide early warning for impending heart attack by localizing regions of abnormal function.

In summary, it is an object of the invention to detect, represent, localize, and measure functional activity of tissues utilizing ionic transmembrane polarization and depolarization. (The presence of significant variations of tissue density or space occupying lesions does not necessarily occur in conjunction with what is detected and represented by the invention).

Other objects of the present invention will become apparent upon reading the following specification and referring to the accompanying drawings in which similar characters of reference represent corresponding parts in each of the several views.

BRIEF DESCRIPTION OF THE DRAWINGS

In the drawings:

FIG. 3 is a curve pairing each value of $\vec{E}$ with the frequency value corresponding to a path length of 12 Å.

FIG. 4 is an operating characteristics table.

FIG. 5 graphically portrays modulation waveform compared to relative surface charge positive ion concentrations occurring during a representative cycle of transmembrane ion depolarization and repolarization.

DESCRIPTION OF THE PREFERRED EMBODIMENTS

Figure 1:
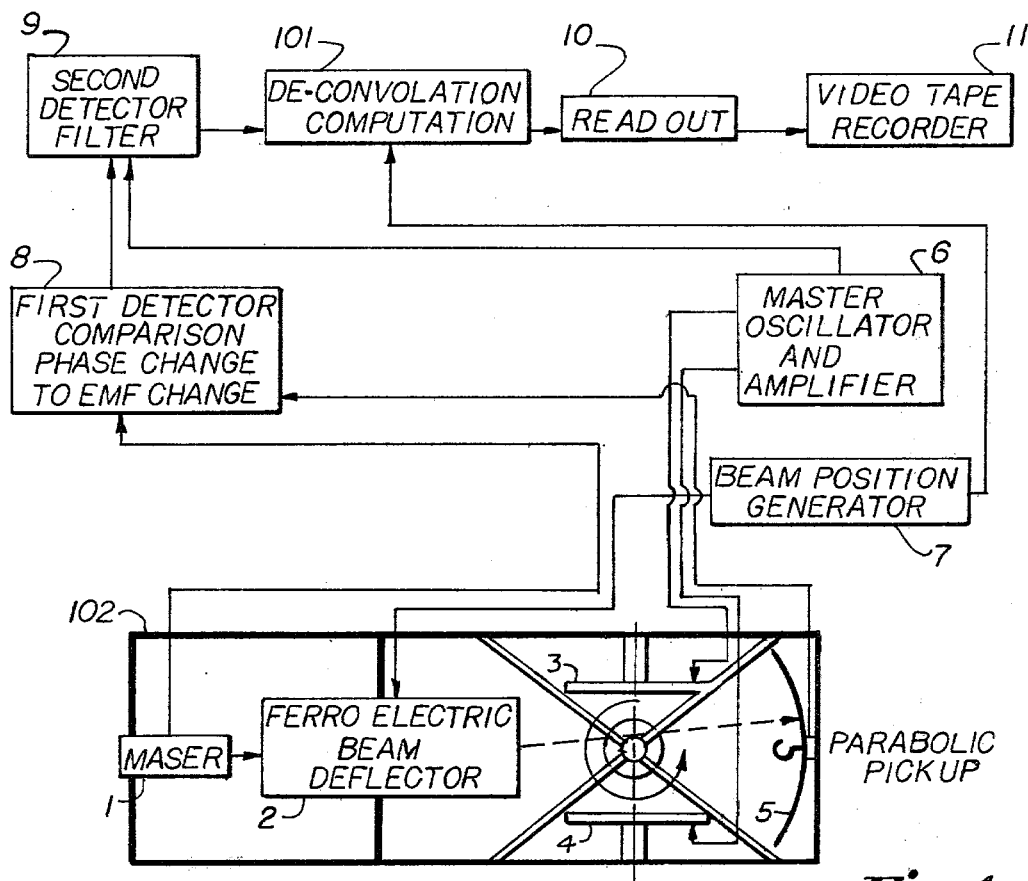
FIG. 1 is a schematic block diagram showing one preferred embodiment of the invention.

Abnormalities of functional capacity and activity (as well as variations of normalcy and individual differences) in tissues utilizing ionic polarization and depolarization across membranes are detected and measured by an electro-optical interaction resulting from the combination of a directional beam from a source of coherent radiation such as a MASER 1, and induced oscillation or vibration of the ionic dipoles or surface change positive ions along the membrane surfaces where positive ions have a free vibrational path in relation to an oscillating exogenons electrostatic field by means of an electrostatic field of adjustable intensity and of adjustable frequency of variation of intensity. The field is established between two plates 3 and 4 of conducting material (such as copper), and the unit thus formed is equivalent to a large capacitor. Separation distance between the plates may be made adjustable by means which will readily occur to one skilled in the art depending on the particular requirements of any selected diagnostic procedure. Direct or alternating current voltage applied to the plates is also variable and determined by other variables such as plate size, separation distance, and workable values that must be less than what will cause discharge between the plates and the danger of shock. If DC is utilized, a minimum value of DC voltage is maintained across the distance between the plates by the output from an amplifier. Output from this amplifier and the Master Oscillator 6 is caused to periodically increase from a set minimum to a maximum voltage, the limit for which is determined by the aforementioned considerations. Frequency of voltage variation is likewise adjustable. Various considerations determine frequency: Resonance for the dipoles spanning membranes of some known homogenous thickness (calculated to be in the range of $4.8 \times 10^8$ Hz for axon fibers of average size having membrane thickness of about 80 Å) provides a frequency that is especially efficient. Plate voltage variation through a wider range of magnitude requires a lower frequency if the maximum discharge rate for the large capacitor generating the oscillating electrostatic field becomes a factor. Frequency of dipole vibration is equal to the frequency of voltage variation applied to the plates.

It is evident that dipole vibration occurs only along a vector that is parallel to the interplate field. The electro-optical interaction producing detection of these dipoles and providing measurement of depolarization activity causes modulation of a directional beam, the orientation of which is perpendicular to the electric field.

The orientation of each of these components in relation to the others must be maintained. Consequently, rotation of a single rigid unit constellated from the large capacitor and the beam around a particular body region being studied is necessary if images corresponding to any chosen discrete plane of cross section in the organic medium are to be available. Images formed in this way can only represent spatially varying measurements. If time variant measurements are to be represented, either a multiple of simultaneous detections produced by an array of beam sources or some approximately equivalent circumstance is necessary. Consequently, rotation of the unit constellated from the large capacitor and the beam around a particular body region being studied or utilization of multiple beam sources is necessary if a planar composite of three dimensions is to be formed.

Referring to FIG. 1, the directional beam source 1 is chosen according to various determinants. A continuous wave output MASER in the millimeter wave range is perhaps ideal. However, other sources may be utilized according to considerations of convenience, exposure time, optimal electro-optical interaction frequency, and energy requirements for penetration.

In view of these considerations, one of the other types of useful sources deserves mention: A CW output LASER operating in the infrared band may be substituted for the MASER. In this case, the system diagram's appearance remains unchanged. However, the antenna pickup located at the focal point of the parabolic reflector is not a detector comparator responding to $\mu$ wave energy or a waveguide input to a nearby $\mu$ wave phase comparator: The pickup is an IR detector comparator or an optical waveguide input to a nearby IR phase comparator. Of course, if the coherent energy source operates in the IR band, the AC coupling connecting the MASER with the phase comparator must be replaced by an optical waveguide. Similarly, coherent radiation in spectral regions other than the preceeding could be utilized if a LASER of the required type were included in the source.

Since phase modulation of the directional beam is due to a reciprocal absorption and reemission process occuring along molecular axes having an orientation parallel to the vibration paths of membrane surface charge positive ions, and this reciprocal process is due to vibration of charged leptons experiencing a directionally reversing acceleration oscillating at the frequency of the electric field which drives it and originates in the directional beam, only plane polarized electromagnetic energy having electric field vectors parallel to the vibration paths of surface charge positive ions is able to participate in the phase modulating interaction. Consequently, optimum use of energy requires that the random polarization of coherent radiation generated by a MASER or a LASER must be plane polarized prior to its propagation through the electro-optically interactive organic medium. Plane polarization of the beam can generally be produced by modulator deflector units of the kind utilized as beam deflectors. However, if plane polarization of the beam is not integral to the operation characteristics of the deflector, it may be independently produced by means such as a quarter wave plate internal to the sources shown in FIG. 2. Beam deflector assemblies may be formed by combining deflectors of two types within each source shown in FIG. 2. An Acoustics-Optical modulator deflector or an Electro-Optical modulator deflector may be combined with a mechanical deflector: The higher frequency AO or EO deflector produces the numerous wider angle excursions each of which corresponds to the length of a single scan line, and the mechanical deflector produces the numerous very small increments (525 is standard) summing to the excursion angle corresponding to all of the scan lines in a single scan.

A detection unit preferably consisting of a directional beam 1, a beam deflector 2, a pair of plates 3, 4 and an antenna 5 to receive the directional beam may be rotated about a patient 1 using, for example, rotatable frame 102. Rotation includes brief stops for the duration of each scan. In this way, functional capacity can be detected in a form that can be represented as discrete points in a given plane.

Reception of the directional beam after it has passed through the body part being scanned is accomplished with any suitable transducer. This system employs one or more parabolic dish antennas, such as the Parabolic Pickup 5.

After the beam has been received, the signal from the Parabolic Pickup is transferred to the First Detector 8 where phase change is determined by a comparison between this signal from the Parabolic Pickup and the signal output from the source, MASER 1. Detector 8 is preferably in close proximity to Pickup 5 and is connected thereto by a short wave guide MASER 1 is connected to detector 8 by means of AC Coupling. Magnitude of voltage from the First Phase Detector 8 corresponds to a combination of the variable to be measured, the product of ion dipole density and volume, and noise produced by random effects. Phase comparison here requires a microwave leveling circuit which is integral with Phase Comparator 8 circuit.

Thus, a function similar to that of a standard automatic gain control is performed and the amplitude of the received signal is modified so as to be comparable to the emitted wave.

A second detector, Second Detector 9, is utilized as a filter to remove noise. Since ion dipoles oscillate at a frequency determined by the Master Oscillator 6, output from the Master Oscillator is utilized at the second phase detector, Detector/Filter 9, so that only in phase average voltage corresponding to the variable to be measured is detected.

Output from the Second Detector 9 is transferred to the Readout 10, which also receives input from the Beam Position Generator 7 allowing position in the plane of scan to be matched with a quantitative indicator. Hence, functional capacity and activity is represented in the form of paired number sets, (x,y), (q), or (x,z), (q), or (y,z), (q), where (q) signifies the quantitative indicator of functional capacity. These number set pairs are time variant. Hence, functional capacity and activity are represented in the overall form (x,y,z,t), (q). The methods of Computer Assisted Tomography represent an already well developed art which is utilized in conjunction with the scanner system presented in the drawing.

Storage of information from the Readout Unit 10 is performed by a Video Tape Recorder 11. Consequently, information acquired by this scanner system can be displayed on a television monitor.

A summary of the system operations is provided in the section entitled "Operations Performed by the Scanner System."

Utilizing only one detector unit, as shown in FIG. 1, will allow functional capacity and activity to be displayed as an image in any given plane representing a perspective projection onto the plane from an origin located at the beam deflector. In this way, an image of functional capacity and/or activity analogous to a simple x-ray picture will be provided, without rotation on gantry 102.

Coupling (not shown) may be utilized in order to reduce energy loss at the interface (between air and body surface), any interposed medium of appropriate refractive index and low loss characteristics would suffice (e.g., a simple waterbag could be used). However, the use of a coupling medium is unnecessary. If power levels are increased, exposure times are decreased. Exposure times may even be reduced to values as low as those utilized in the potentially hazardous scanner systems using ionizing radiation (beams of electromagnetic energy perhaps in the x-ray band, or even particle beams).

In relation to the directional beam's function in detection, attenuation and heat loss do not interfere. Phase change between the directional beam and a reference occurring at a predetermined modulation frequency is measured as an indicator of functional capacity and activity. However, attenuation of the directional beam is not measured. Power levels utilized for the directional beam are not high. Available sensitivity for the beam detector is sufficiently high so that attenuation does not hinder response.

Detection of functional capacity and activity does not require that a microwave signal entering the body will suffer as its principal distortion source the effect of vibrating ionic dipoles. The effect measured in this scanner system is the amount of interaction between oscillating ionic dipoles (positional vibration of ions in relation to membrane surfaces) in a volume's locus and electromagnetic energy propagating through the locus of that volume. Other tissue characteristics such as dielectric constant variability are not detected since their contributions to phase change in the directional signal are not modulated effects oscillating at the frequency predetermined by the Master Oscillator 6. Regional variations of tissue composition and corresponding dielectric constant variations exist. However, these variations do not reduce the accuracy of the detection mechanism since the amount of phase change is not used to measure capacity or activity. The total amount of phase change occurring along a given path is neglected at the filter: Phase change itself is not measured. Only modulated phase change at the frequency of vibration for the vibrating ionic dipoles is measured. The frequency of phase change modulation is equal to the frequency of intensity variation of the interplate electrostatic field. In order to contribute to measurements of functional activity and capacity, the oscillating phase changes in the directional beam must be in phase with the oscillations of electrostatic field intensity. Of course, attenuation such as that corresponding to heat generation in diathermy is not a contributing factor in relation to the electro-optical interaction (phase alteration) from which measurements are derived. In consideration of the preceding, it is evident that regional variations in the amplitude distribution of microwave energy (such as those presented by Robinson, et al) and phase change related effects due to regional variations of dielectric constant do not reduce the accuracy of the detection mechanism utilized in this scanner system.

In relation to diagnosis of regional functional capacity or activity abnormality that is stable in relation to values for ambient tissue which are greater than, less than, more variable than, or less variable than detector measurements corresponding to the regional abnormality, pathology is indicated by a relative difference of capacity or activity only. This relative difference appears in the scan image or visual display as a contrast between the region of pathology and its surrounding matrix. As is the case with a simple x-ray, interpretation of a visual representation depends upon the diagnostic skill of the interpreter and will often be a supplement to a clinical evaluation.

Vibrating ionic dipoles are detected. These dipoles are produced by an active transmembrane ion separation process. This separation process is a characteristic of only a very limited number of cell types: neurons and muscle cells are essentially the only two types of cells in this category. Compositional variations of tissue encountered by the directional beam along its propagation path do not reduce the accuracy of measurement. Transmembrane ionic vibrations corresponding to neuron tissue are neither inundated to the point of insignificance nor camouflaged by the peripheral presence of muscle tissue: The EEG is possible even though an EMG can be performed in the region of the head. Ion induced current is greater for muscle than for neural tissue: potentials on the EMG are much greater than those on the EEG. Potentials recorded on the EKG are also high compared to those recorded on the EEG. However, the EEG remains feasible. Since the relative contributions of ionic dipoles to measurement values in the scanner system correspond to the relative contributions of the appropriate type in the EEG, EKG, and EMG, the adequacy of magnitude and circumstances in relation to differential detection for the preceding set requires that magnitude and circumstance of detected events are adequate to allow differential detection in the scanner system. Additionally, when muscle in the head region is inactive, the only $\Delta q$ values result from functional activity in neural tissue.

If a plane of scan is viewed, the image can be spatially analyzed. Muscle tissue can be readily separated from neural tissue since muscle tissue appears peripheral to neural tissue.

What is most intrinsic, essential, and central in this device is its ability to provide an immediate and exclusive visual representation of the condition and state (which might include abnormality) of neutral tissue, cardiac tissue, smooth muscle, or skeletal muscle. This is possible only because functional capacity and activity in the form of transmembrane ion polarization and depolarization provides the only measured source of change in the directional beam. The composition of the image produced in an indicator of localized variation.

Since phase change alone is not measured, density changes and density changes combined with dielectric constant changes due to tissue composition do not reduce the accuracy of measurement.

Oscillating refractive index effects due to vibration of ions other than transmembrane surface charge ions exist but are unable to reduce measurement accuracy by modulating the directional beam at an in-phase vibrational frequency corresponding to the interplate field intensity oscillation.

Consideration of Noise Generation Internal to the Organic Medium

Charge bearing entitles other than transmembrane ionic dipoles exist. Some of these are able to respond to the oscillating interplate electric field by migrating along a path parallel to the interplate field vector. However, none of these charge bearing entities is able to respond to the exogenous electric field's DC or AC fluctuations with either rapidity or summating consistency of refractive index altering effect comparable to the response produced by positionally vibrating surface charge positive ions ($Na+$, $K+$, and traces of others EG: $Mg^{++}$ and $Ca^{++}$) contiguous to membranes having a phospholipid constituency.

Free ions in the blood stream move freely in the interplate field. However, in the DC modes these ions move in only one direction. Localized electric fields demonstrating either stable configurations or stable variation patterns having stable ranges of values capable of directly or indirectly opposing ion motion induced by the exogenous electric field do not exist. Hence, these ions are unable to respond to exogenous unidirectional field intensity variations by vibrating positionally even through the exogenous field has some fixed frequency of variation through a preset range. These ions are able to respond to these DC field oscillations only by drifting at an oscillating rate in one direction. Additionally; these ions are not concentrated in the regions of any surfaces in relation to which they could produce an oscillating value of refractive index even if they were able to vibrate positionally. Hence, when these free ions do vibrate positionally in the AC modes, they do not produce any significant oscillation in the refractive index interacting with the directional beam. Some platelets, erythrocytes, leukocytes, albumins, globulins and various classes of unlisted blood proteins (e.g., hormones) drift through the interionic spaces between small ions which are occasionally able to vibrate in unison with the oscillating interplate AC field. However; these blood components are randomly bending and rotating as they travel and are consequently unable to maintain any fixed alignment in relation to the exogeneous electric field. Since various fixed alignments of certain molecular axes along which dipole moment oscillations can occur in response to positional vibrations of charged particles are necessary if phase modulation of the directional beam is to be produced, these blood components are unable to produce phase modulation at the interplate oscillation frequency even though they occasionally approach positionally vibrating small ions.

Blood proteins are able to migrate in an electric field. This fact is utilized in electrophoresis separation methods. However, proteins are by definition generally regarded as polypeptides having a molecular weight of 6000 AMU or more. It is evident that these molecules are unable to undergo rapid reversals of direction corresponding to a rapidly oscillating AC interplate field. They may undergo slight diametric expansion and contraction. However, even this response to an AC interplate field is unable to slightly influence phase modulation of the directional beam since random molecular rotation and bending precludes any stable frequency dependent responses.

Blood components such as proteins are capable of very slow vibratory motions having very limited path lengths. However, they are unable to produce phase modulation of the directional beam even at very low interplate field intensity oscillation frequencies since they are not concentrated near any surfaces in relation to which their vibratory motion could be positional: They are unable to produce any refractive index oscillation.

Interstitial $Na^+$ and $K^+$ ions abound in an aqueous medium. However, the effects of vibratory motion among these are consistent with those of transmembrane surface charge positive ions. In fact, the vibratory motions of these facilitate the motions of surface charge positive ions since surface charge positive ions reciprocally follow these or are chased by these due to diffusion displacement.

In summary, phase modulation is produced by positional vibration of ions. Only membrane surface charge positive ions are able to participate in this process.

The explanation given for the insignificance of apparent sources of noise within the organic medium that might seem able to interfere with measurement accuracy during scanner operation in the AC modes fails to be comprehensive in only two instances:

(1) Free ions are able to vibrate near the surfaces of all cell membranes contacting the interstitial aqueous medium. Glial cells, the outermost laminations of the myelin formed from Schwann cells, and cells forming the blood vessel walls account for virtually all cell membranes in this category. These cell membranes contain phospholipids. However, these types of cells do not generate high concentrations of transmembrane ions and therefore do not generate transmembrane electric fields.

(2) Surface charge ions are highly concentrated along the membrane surfaces of astroglia. However, these cells do not depolarize. These cells are an exception to statement (1) above in relation to neuroglia.

The cell membranes of cell typed listed in instance (1) produce only small phase modulation effects in the directional beam since they do not maintain high concentrations of polarized surface charge ions. They respond only to free ion vibrations in the regions of their plasma membrane surfaces. Membranes of cells of the type listed in instance (2) produce phase modulation in the directional beam as efficiently as membranes of neurones in the polarized state.

Noise of the type produced by instance (1) cells during the AC modes of scanner operation does not affect depolarization measurements. Noise of this type obscures measurement of polarization state values by less than one percent since the transmembrane electric fields of $\approx 10^5$ Volts/cm which maintain the surface charge of polarized membranes are absent. If the ratio of $\vec{E}/\gamma$ is increased far beyond the values present in the curve corresponding to a 12 Å patch, these noise effects are markedly increased. Since these noise effects are not time variant a constant spatially patterned matrix of C A T numbers can be recorded for this stable noise distribution. This matrix is a high contrast, high resolution noise distribution matrix. If the ratio of $\vec{E}/\gamma$ is then reduced to a value closer to one on the 12 Å path length curve, and the intensity values from a stable low contrast, low resolution matrix for the constant background values corresponding to the absence of any depolarization are spatially distributed in the fixed configuration of the high contrast noise matrix (Intensity values from the low contrast, low resolution matrix are substituted for intensity values in the high contrast high resolution matrix.), after which the resultant synthetic C A T matrix is returned continuously to the Second Detector Filter, during functional activity scanning, in phase with the Master Oscillator and voltage inverted, noise corrected input to the Analog-Digital Converter is obtained.

Phase modulation due to the astrocytes is not actually noise. These cells do not depolarize. However, they do contribute to the brain's electric field in close proximity. These cells are very small and sparsely distributed compared to neurones.

The effect of astrocytes on phase modulation in the directional beam is negligibly small and consequently does not interfere with measurement accuracy.

The previously described high contrast, high resolution noise matrix generated by increasing the ratio of $\vec{E}/\gamma$ to values corresponding to path lengths $>> 12$ Å is useful in itself. This time invariant, spatially variant distribution of phase modulation in the directional beam can be transferred to a TV monitor separate from the TV monitor which visually presents functional capacity and activity in cross section. It provides an image almost exclusively representing tissue other than membranes that transpose ions. If a DC mode matrix of functional capacity measurement numbers is preserved in spatial configuration but altered by the substitution of image intensity values derived from an AC mode scan having values of $\vec{E}$ and $\gamma$ close to those presented on the 12 Å path length curve, and this synthetic time invariant matrix is continuously subtracted from the high contrast high resolution time invariant AC mode noise matrix utilizable for noise correction in the AC modes of operation, then a matrix of CAT numbers representing all tissue or tissue surfaces, other than impulse generating membranes, contacting a fluid boundary of a solution containing free ions is produced. This matrix may be transformed into an image on the TV monitor separate from the one presenting functional capacity or activity. To perform the measurement value subtraction, the synthetic constant value CAT matrix may be transferred to the Second Detector Filter, in phase with the Master Oscillator's output and voltage inverted. This feedback loop will factor out the measurement variability corresponding to membranes that polarize and transpose ions.

Image subtractions or measurement subtractions can be readily performed within the computer itself, putting to use the computer memory, in the form of matrix subtractions. Consequently, a feedback loop from the computer to the Second Detector Filter requiring a Digital Analog signal conversion is not shown in FIG. 2.

Power levels for the beam source are much lower than those used to produce diathermy. For example, Robinson, McCulloch, and Edelsac describe microwave heating of malignant mouse tumors by a 2450 $MH_z$ diathermy machine operating in the power output range of 200 watts. The beam utilized in the scanner system utilizes a MASER or a LASER in the frequency range above 30 GH$_z$ operating in the power output range of 0.001 watt. Currently available sensitive low noise detectors (mixer-diodes) such as those made by Mullard Inc. of England and Microwave Associates of Mountain View, Calif., render the use of potentially harmful wattages of microwave radiation unnecessary and undesirable. The FCC has determined that continuous exposure to microwave radiation at power levels $\geq$ 10 mW for a period of years may cause humans to experience sluggishness. Power levels required by the scanner system are well below this limit.

Operations Performed by the Scanner System

1. The change in phase of the 1 mm wave (or a wave of some other length) is seen as a change of voltage at the first detector input as this detector compares phase information supplied by the pickup antenna with input from a direct coupling to the MASER (or other source of e.m. energy). This voltage will oscillate at the rate set by the master oscillator since this oscillator also controls the field modulation amplifier and the field across the plates.

2. Since the phase shift of the 1 mm wave by these means will be less than 90°, the magnitude of voltage from the first phase detector will correspond to (V) (MDPD) where V represents volume of ionic dipoles penetrated by beam; and MDPD represents modulated dipole density) encountered by the beam at any particular position in a plane, xy, yz, or xz of scan as well as noise.

3. The master oscillator output is also used at the second detector/filter where only in phase average voltage will be detected. Hence, (V) (MDPD) will be detected but noise caused by unmodulated moving material encountered by the beam will be eliminated.

4. As the beam is scanned across the subject in the plane normal to the beam, output from the beam position generator along with the varying second detector output is conveyed to a video tape recorder for later interpretation.

Reference is made to FIGS. 3–5, which show representative results of this invention.

The curve in FIG. 3 displays the frequency of oscillation for the Master Oscillator/Amplifier unit 6 which must be applied to the plates 3, 4 if the electrostatic field intensity between the plates has one of the represented values. (Values derived from this curve correspond to a displacement path length of 12 Å for the positionally vibrating surface charge ions.)

FIG. 4 presents characteristics and ranges of values for some of the system's components. Listed here also are some examples of use of the apparatus and method. The example voltages correspond to an interplate separation distance of 40 cm.

The interplate separation distance is adjustable and the value represents the general case.

The table in FIG. 5 presents relative concentration values for Na$^+$ and K$^+$ ions on opposing sides of the membrane. The membrane is represented by the line transecting the blocks which graphically represent concentrations of these ions. Blocks above the separating line represent surface charge positive ion concentrations along the outer membrane surface. Blocks below the separating line represent surface charge positive ion concentrations along the inner membrane surface. The values labeled Outer Charge apply to the transmembrane electric field and the sign of voltage polarity refers to the outer membrane surface. Modulation waveforms are explained in the Operation Mode Summary which follows. The amplitudes of these waveforms are proportional to the vibrationally available surface charge ion concentrations and inversely proportional to the transmembrane electric field intensity opposing displacement of these ions away from the membrane surface.

Operation Mode Summary

Referring to FIG. 4, modulation waveforms are based on the assumption that the time interval during which + ions diffuse across the membrane to replace the displaced + surface charge ions is less than the time interval required for transmembrane + ion diffusion to significantly counteract the Δn resulting from displacement of + surface charge ions. This assumption is correct in relation to both the AC 2 and the DC 2 modes of operation.

During the DC 1 and the AC 1 modes of operation, the time interval for $\frac{1}{2}$ cycle is sufficient to allow $\frac{1}{3}$ of the K$^+$ ions to diffuse across the open membrane if these K$^+$ ions diffuse from one membrane surface to the other at their maximum rate. This effect effectively cancels the induced oscillation of Δn between 0.8 and 1.1 msec as well as between 2.0 and 4.0 msec. Between 1.7 msec and 2.0 msec, this effect produces some cancellation of the oscillating Δn. Between 1.1 and 1.7 msec, this cancellation effect is virtually absent. Since depolarization begins at 0.5 msec, phase modulation due to the cross sectional area across the membrane in a plane parallel to the interplate electric field and perpendicular to the propagation path of the directional beam is virtually zero during 2.3 msec of the 3.5 msec depolarization interval. Between 0.5 and 0.8 msec, the amplitude of phase modulation is very small and in the presence of this effect, it is zero. Hence, the interval during which phase modulation produced by the open membrane is either zero or virtually zero amounts to 2.6 msec. Some reduction of phase modulation to a level equal to the level occurring during the polarized state occurs during 0.3 msec of the depolarization interval. Phase modulation at a level higher than that for the polarized resting state occurs for only 0.6 msec. Since phase modulation during depolarization is less than during polarization for 2.6 msec (when it is $\approx$0), more than during polarization for 0.6 msec, and equal to the polarization level for 0.3 msec, the net effect on phase modulation (in the DC 1 and the AC 1 modes) of depolarization is a reduction to zero for a 2 msec interval. Hence, a decrease of phase modulation indicates depolarization having increased: Decreasing phase modulation indicates increasing functional activity.

In the AC 2 and DC 2 modes of operation, increasing phase modulation indicates increasing functional activity.

The value of γ listed on the table of operating characteristics is $\approx$2.3 GHz. This is the frequency of interplate electric field oscillation at which the displacement rate of surface charge positive ions traveling away from the membrane surface due to the exogenous electrostatic field along a 12 Å path during the time interval of $\frac{1}{2}$ cycle would equal the displacement rate of these ions through 12 Å due to diffusion in the aqueous interstitial medium.

"Electromagnetic radiation" as used herein includes what are commonly termed laser and maser beams and equivalents.

Concerning Various Modes of Operation or use of the Invention

1. If the scanner is to be operated for an extended period of time, polarity of the DC output from the Master Oscillator and Amplifier must be periodically reversed. This reversal is performed in order to counteract the accumulation of oppositely charged free ions (due to their forced migration resulting from the applied electric field) on opposing sides of the body. Of course, if the periodicity of polarity reversal of the direct current applied to the plates is rapid, field variation corresponding to AC is produced.

2. Frequency of oscillation for the output from the Master Oscillator can be tuned through the range of frequencies corresponding to the range of resonance frequencies for fiber membrane thicknesses from the smallest value of ionic dipole separation distance to the greatest value. Peak values of energy absorption due to resonance absorption can then be graphically represented as a function of frequency. This will portray a measurement of the number of functional membranes of any particular thickness. The amount of resonance energy absorption for any particular frequency (where measuring the number of functional membranes utilizes a good approximation iff the resonance frequency curve is sharp) is directly proportional to the number of functional membranes having a thickness for which resonance occurs at the particular frequency being considered.

Of course, all types of rapid charge reversal on a capacitor require some means for removing the sequentially alternated polarities of charge. In general, charge variation on a capacitor at a rapid rate requires utilization of a bleeder. The bleeder is intended to be included in the Master Oscillator and Amplifier unit.

Detection

1. The first detector 8 is a phase comparator. It includes the necessary microwave leveling circuit. The received signal from the source is compared to what it would be in the absence of the organic medium through which it has propagated. Phase change is converted to EMF change which is transferred to the second detector.

2. The second detector 9 serves as a filter. The amplitude of the EMF received from the first detector 8 corresponds to the amount of phase difference (a measure of delay time) between the received signal which has propagated through an organic medium and a reference which corresponds to the same signal in the absence of an organic medium. A portion of the amplitude of the EMF received from the first detector is oscillating at the frequency of the master oscillator 6 and is in phase with the output from the master oscillator. The value of this portion of the amplitude and only the value of this portion of the amplitude corresponds to the amount of phase modulation induced by the oscillating electrostatic field via vibrating ionic dipoles in the field.

3. Only the portion of the EMF amplitude corresponding to the amount of phase modulation is equivalent to the value (q), the scaler value in the field defined by (x, y, z, t) (q).

4. Only the portion of the EMF amplitude corresponding to the amount of phase modulation is transferred from the second detector to the analog digital converter 10. Time variant changes in the value of amplitude transferred from the second detector to the analog digital converter are equivalent to $\Delta q$.

Referring now to FIG. 1, hereinafter discussed in detail, each unit designated $S_1, S_2, \ldots S_n$ is a source of microwave radiation in the form of a scanned directional beam. Each source includes a MASER and a beam deflector. If the beam deflection is fanned through an angle described in a plane that is perpendicular to the orientation of the electric field vector in the directional microwave beam, and the plates 3a, 4a are oriented in planes that are perpendicular to what would be considered the plane of the paper of the drawing, then the beam deflector could be of the reflector type, but could not be of the electro-optical type shown in FIG. 1 unless the electric field polarity of the directional beam is rotated, after deflection, by 90°. As in considering FIG. 1, the electrostatic field vector between the plates must be parallel to the electric field vector in the beam of microwave radiation.

The Timer 15 is used to sequentially switch from one source location, $S_1, S_2, S_3, \ldots S_n$ to another through an extremely rapidly repeating sequence.

If only values of q corresponding to the polarized resting state of membranes that polarized and transposed ions are represented for some number of scans from a particular location, then information needed for image reconstruction of the type utilized in CAT scanners can be gathered by rotating a unit of the type shown in FIG. 1 through an angle of 180° in increments of several degrees. Whether these values are maximum values or minimum values is listed in the Operation Mode Summary. In this case, the image obtained represents functional capacity in body organs scanned: Functional activity is not represented. Rotation of the scanning unit must pause during each scan or series of scans from a particular orientation. The scanning operation may be summarized as follows:

1. Output from the second detector (filter) is passed through a log amplifier and digitalized.

2. The digital signal is utilized for image reconstruction.

3. After a complete scan the reconstructed image (equivalent to a matrix of CAT numbers) resides in the computer memory or on a magnetic disk.

4. To display this matrix on a TV monitor, or to record it on a high speed VTR, the digital numbers are converted to an analog signal and the signal is continually refreshed to provide an image that is flicker-free.

Figure 2:
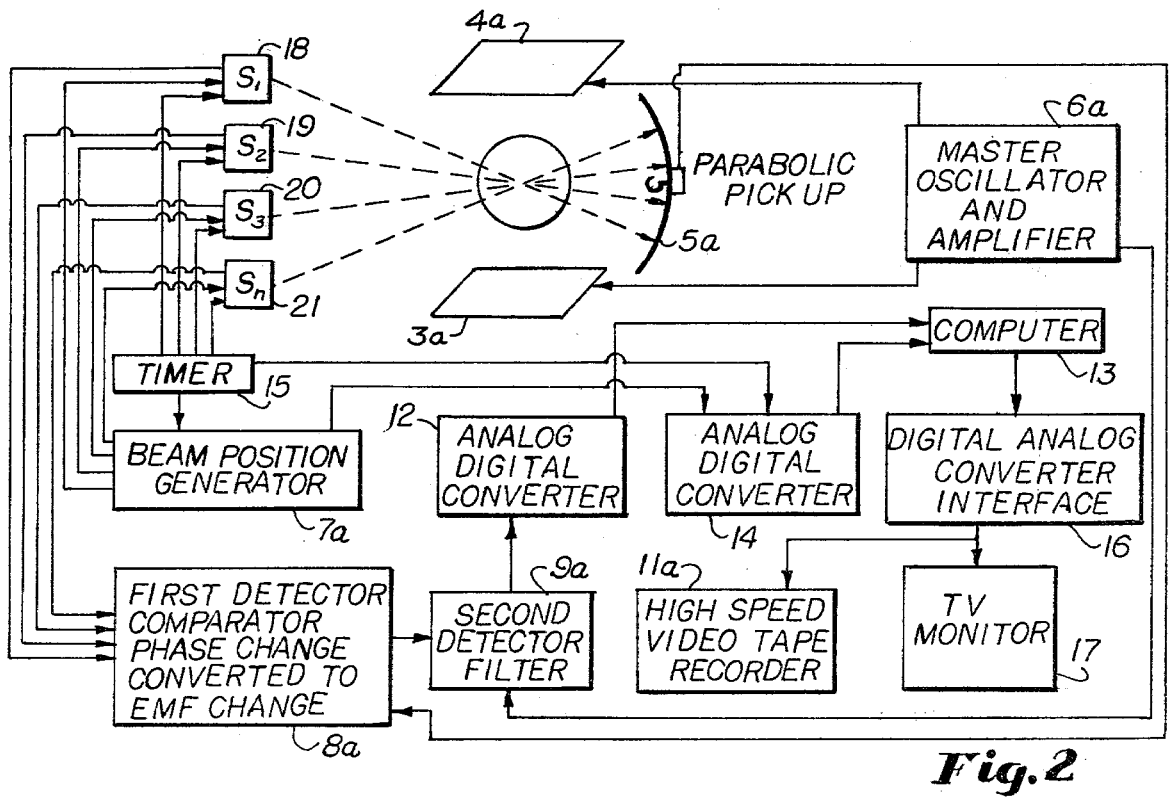
FIG. 2 is a view similar to FIG. 1 of another preferred embodiment.

Multiple Detectors or "Simultaneous Detectors" must be utilized (as shown in FIG. 2) in order to acquire information necessary for image reconstruction of time variant (functional) changes (activity), $\Delta q$ values, if these changes in the value of (q) are not organized in predictable, simple, repetitive sequences. A multi-detector system will allow recording information of this type in the overall form (x, y, z, t) (q) where $\Delta q$ represents $q_2 - q_1 = f(t_2) - f(t_1)$.

If the discrete plane to be imaged is determined prior to recording, information can be recorded directly on a high speed VTR and use of the computer memory or magnetic disks can be bypassed. Numerous timer generated scans provide information from all of the multiple detectors which is combined into a single composite unit (equivalent to a matrix of CAT numbers). The time required to generate one of these composite units is the time interval represented by each single scan image. The smallest possible recorded value for $\Delta q = f(t_2) - f(t_1)$ where $t_2 - t_1$ = amount of time required to generate one of these composite units. Sequences of these composite units are recorded to represent functional activity. Durations of these recorded sequences may be extremely long compared to the time required to generate a single composite image represented in the equivalent of a single matrix of CAT numbers. Hence, an extended series of matrices may be generated which could become cumbersome if stored in the computer memory or on magnetic disks. These storage means might be utilized. However, direct recording of chosen image sequences in chosen discrete planes of the VTR might often be convenient.

Performance characteristics of electro-optical beam deflectors are perhaps optimum. However, use of the computational unit requires use of "multiple detections" which are processed as though occurring simultaneously. These multiple detections require multiple sources located at various locations having different orientations in relation to the object being scanned. These sources are placed within a range of scan orientation angle variation of 180°. Efficient use of the interplate electostatic field is provided if the plates are arranged so that the electrostatic field vestor is perpendicular to the plane of beam sweep, and the electric field vector of the beam is parallel to the electrostatic field vector. Since beam deflection of the electro-optical type utilized in a ferro-electric deflector requires the electric field vector of the beam to be parallel to the direction of sweep (to be in the plane of sweep angle), a beam deflector of the reflector type might be utilized.

In relation to the description of scanner use in the AC mode of operation, the frequency of phase modulation should be defined as the rate of complete polarity reversal cycle generation by the Master Oscillator, Amplifier unit.

DIAGNOSTIC EVALUATION OF THE HEART

An application of the scanner

1. In the resting state, myofibrils of cardiac muscle maintain transmembrane ion polarization.
2. Preceding and initiating contraction of the myofibril, transmembrane ion depolarization occurs.
3. The cycle of events of which the alternating myofibril states of relaxation and contraction is a function is the reciprocal transition between myofibril transmembrane polarization and depolarization of ions.
4. The scanner system will detect and display that aspect of cardiac functional activity defining the independent variable. Alternation of state of the myofibril between contraction and relaxation constitutes the dependent variable.
5. The development of heart disease in the form of localized regions of ischemia which may eventually produce myocardial infarctions, or heart attacks can be detected by the scanner system. The specific three dimensional locations of these regions of ischemia can be displayed on three television monitors, xy, yz, xz plane.
6. Since cellular malfunction as a consequence of ischemia will develop prior to cellular death, detecting regions of decreasing cardiac functional activity due to increasing ischemia will allow the discovery of impending heart attacks before they occur.
7. It is to be hoped that methods such as surgical boood vessel rerouting will be utilized in response to the early detection of impending infarction allowed by this scanner to prevent the actual occurrence of heart attacks.

Diagnostic evaluation of smooth muscle and skeletal muscle is another application of the scanner system utilizing points 1-4 of the presentation of diagnostic evaluation of the heart.

Conduction abnormalities of the heart and muscle tissue in general can be detected and displayed by the scanner system.

Description of FIG. 2

As diagramed in FIG. 2, the scanner system does not include the Readout 10 unit shown in FIG. 1. In FIG. 2, the Readout unit is replaced by an Analog-digital Converter 12 which digitalizes the output from the Second Detector Filter 9a and provides input to the Digital Computer 13. A second Analog-Digital Converter 14 receives input from the Timer 15 which clocks the Beam Position Generator 7a and determines which of the multiple sources 18–21 . . . is activated at any given time. The second Analog-Digital Converter 14 also receives input from the Beam Position Generator 7a. Digitalized input to the Digital Computer 13 from the second Analog-Digital Converter 14 locates the coordinate position corresponding to the scalar magnitude output from the first Analog-Digital Converter 12. Output from the Digital Computer 13 is converted into analog values by the Digital-Analog Converter Interface 16 which provides the signal that is displayed on the TV Monitor 17. The signal provided by the Digital-Analog Converter Interface 16 can also be recorded on a high speed Video Tape Recorder 11a.

The MASER 1 and the Ferro Electric Beam Deflector 2 shown in FIG. 1 are not shown in FIG. 2. In place of these units, FIG. 2 shows the multiple sources $S_1$, 18, $S_2$, 19, $S_3$, 20 and $S_n$, 21. $S_n$ is the nth source in a set (1, 2, 3, . . . n) including any number of sources useful for generating a matrix of CAT numbers. Each source includes a generator of narrowbeam coherent electromagnetic energy such as a MASER and an xy deflector assembly.

In both FIG. 1 and FIG. 2, the distance between the receiving transducer, the Parabolic Pickup 5 and the First Detector Comparator 8 is restricted. The first Detector Comparator 8 can also be located just behind the parabolic reflector 5 or in front of the reflector, between the antenna and the inner reflector surface.

Many of the components of FIG. 2 at least generally resemble those of FIG. 1, and corresponding parts are marked with the same reference numerals followed by the subcript a. Electromagnetic energy emitted by a source, which energy has a waveform that is nearly perfect (lacking deviations from or distortions of the form of the omitted energy's waves) is propagated along a unidirectional straight line path. This propagated energy may be called a beam. The waves of all of the emitted energy must be in phase with one another. Currently, waveforms of the kind in reference here are found in the coherent wave radiation emitted by LASERS and MASERS. "Electromagnetic radiation" as used herein means use of a beam source of electromagnetic radiation such that differential of phase modulation as specifically modulated according to the description given in the specification occurs. Further, electromagnetic energy emitted by a source, which energy has either a summated waveform corresponding nearly exactly to the sine wave standard or a summated waveform deviating from the sine wave identically for each of any two waves compared for phase relationship is propagated along a unidirectional nearly straight line path. This propagated energy may be called a beam. Currently, the sine wave form of summation (all waves must be congruent) found in the coherent wave radiation emitted by LASERS and MASERS is included.

The term "electromagnetic radiation" as used in the accompanying claims means such wave radiation and equivalents.

What is claimed is:

1. A method of diagnostic radiological analysis of a body part comprising the steps of:
   (a) producing a coherent directional beam of electromagnetic radiation;
   (b) locating the body part to be studied between two chargeable plates;
   (c) producing an electrostatic field between said plates and adjusting the intensity and frequency of variation or oscillation of intensity of said field;
   (d) propagating said beam through said body part; and
   (e) producing an image of the received beam.

2. The method of claim 1 wherein the step of producing a beam comprises generating a beam of microwave frequency using a MASER.

3. The method of claim 1 wherein said body part comprises the human brain and said step of producing an image comprises forming an image of ionic dipole density variations within the human head, and which further compares regional abnormalities to images of space occupying lesions and other abnormalities of body part tissue density variation.

4. The method of claim 1 wherein said body part comprises the human heart and which further comprises the step of forming an image of ionic dipole density variations within the heart and detecting localized abnormalities evidenced in said image.

5. The method of claim 1 which further comprises scanning said directional beam through said body part.

6. The method of claim 5 in which said scanning step is performed by sequentially producing a plurality of said beams from discrete locations around an arc having a focus at said body part.

7. Apparatus for diagnostic analysis of a body part comprising:
   generating means for a coherent directional beam of electromagnetic radiation,
   a pair of parallel metallic plates spaced apart to receive said body part,
   means for producing an oscillating electrostatic field between said plates and for adjusting the intensity and frequency of variation or oscillation of intensity of said field,
   a transducer for receiving said beam after it has passed between said plates and said body part, and means for producing an image of the beam received by said transducer.

8. Apparatus according to claim 7 which further comprises means for deflecting said beam whereby to scan at least a portion of said body part.

9. Apparatus according to claim 8 in which said last-mentioned means is a ferro-electric beam deflector.

10. Apparatus according to claim 8 in which said means for producing an image comprises first detector means receiving signals both from said generating means and said transducer and comparing said signals for phase change, second detector means receiving signals both from said means for producing an oscillating field and from said first detector means and filtering out noise from said signals.

11. Apparatus according to claim 7 in which said generating means is of microwave frequency 12. Apparatus according to claim 11 in which said generating means ia a MASER.

13. Apparatus according to claim 10 which further comprises a plurality of said generating means spaced apart and all directing their beams to pass between said plates, and timing means for sequentially activating each said generating means, said means for deflecting said beam controlling all of said generating means.

14. Apparatus according to claim 7 which further comprises a first analog to digital converter receiving a signal from said second detector means, a second analog to digital converter receiving signals from both said timing means and said means for deflecting said beam and emitting a signal indicative of which of said beam generators is activated, a digital computer comparing the outputs of both said analog to digital converters to locate coordinate positions corresponding to the scaler magnitude output from said first analog to digital converter, a digital to analog converter receiving the output of said computer and means for displaying the output of said last-mentioned converter.

15. Apparatus according to claim 14 which further comprises a recorder for the output of said last-mentioned converter.

* * * * *